(12) United States Patent
Han et al.

(10) Patent No.: US 12,721,987 B2
(45) Date of Patent: Sep. 1, 2026

(54) ACOUSTIC TWEEZER

(71) Applicant: KOREA INSTITUTE OF SCIENCE AND TECHNOLOGY, Seoul (KR)

(72) Inventors: Sungmin Han, Seoul (KR); Jeong Min Heo, Seoul (KR); Inchan Youn, Seoul (KR); Won Seok Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 587 days.

(21) Appl. No.: 18/330,751

(22) Filed: Jun. 7, 2023

(65) Prior Publication Data

US 2024/0091516 A1 Mar. 21, 2024

(30) Foreign Application Priority Data

Sep. 19, 2022 (KR) ........................ 10-2022-0117645

(51) Int. Cl.
*A61B 17/30* (2006.01)
*A61M 37/00* (2006.01)
*B06B 3/00* (2006.01)

(52) U.S. Cl.
CPC ......... *A61M 37/0092* (2013.01); *A61B 17/30* (2013.01); *B06B 3/00* (2013.01); *B06B 2201/76* (2013.01)

(58) Field of Classification Search
CPC ...... A61M 37/0092; A61B 17/30; B06B 3/00; B06B 2201/76; B06B 1/0207; B01L 3/502761; A61N 7/02; A61N 2007/0021; A61N 2007/003; A61N 2007/0073; A61N 2007/025; A61N 2007/027
(Continued)

(56) References Cited

U.S. PATENT DOCUMENTS 3,948,248 A * 4/1976 Zuckerman .............. A61B 8/10 600/463
4,086,917 A * 5/1978 Burks .................. A61B 5/4362 600/453
(Continued)

FOREIGN PATENT DOCUMENTS

KR 10-1860198 B1 6/2018
KR 10-2051188 B1 1/2020
(Continued)

OTHER PUBLICATIONS

Junfei Li et al., "Three dimensional acoustic tweezers with vortex streaming," Communications Physics, 2021, 4:113.
(Continued)

*Primary Examiner* — Isiaka O Akanbi

(57) ABSTRACT

An acoustic tweezer is disclosed. The acoustic tweezer includes a function signal generator configured to generate a function signal for an ultrasound signal, a power amplifier configured to amplify the ultrasound signal based on the function signal, and an ultrasound transducer of a single channel in which a hologram thin film having different thin film thicknesses for each region is attached to an ultrasound oscillating surface of the ultrasound transducer, and the ultrasound transducer is configured to generate a plurality of ultrasound signals having different phase differences by allowing an oscillated ultrasound signal to pass through the hologram thin film.

8 Claims, 7 Drawing Sheets

(58) Field of Classification Search
USPC ................ 356/502, 121, 213, 434, 432, 337
See application file for complete search history.

(56) References Cited

U.S. PATENT DOCUMENTS

| | | | | |
|---|---|---|---|---|
| 5,873,845 | A * | 2/1999 | Cline | A61N 7/02 601/3 |
| 8,469,893 | B2 * | 6/2013 | Chiang | G01S 7/52073 600/407 |
| 8,512,250 | B2 * | 8/2013 | Quistgaard | A61B 8/4483 600/407 |
| 10,704,021 | B2 * | 7/2020 | Lipkens | C12M 33/08 |
| 12,318,635 | B2 * | 6/2025 | Rousso | A61N 7/02 |
| 2005/0148875 | A1 * | 7/2005 | Sato | A61B 8/06 600/453 |
| 2005/0206479 | A1 * | 9/2005 | Nguyen | H03H 3/0072 333/186 |
| 2009/0112098 | A1 * | 4/2009 | Vaezy | A61N 7/02 600/459 |
| 2010/0267158 | A1 * | 10/2010 | Chou | B82Y 35/00 216/13 |
| 2013/0047728 | A1 * | 2/2013 | Cochran | G10K 15/02 73/570.5 |
| 2013/0120322 | A1 * | 5/2013 | Tanaka | G06F 3/043 345/177 |
| 2013/0330247 | A1 * | 12/2013 | Wilson | G01N 1/286 422/504 |
| 2015/0105658 | A1 * | 4/2015 | Park | A61B 8/481 600/431 |
| 2016/0243234 | A1 | 8/2016 | Healey et al. | |
| 2018/0071505 | A1 * | 3/2018 | Lo | A61K 9/0009 |
| 2018/0228464 | A1 * | 8/2018 | Yang | A61B 5/0062 |
| 2019/0017924 | A1 * | 1/2019 | Duffey | G01N 29/2425 |
| 2019/0201326 | A1 | 7/2019 | Airan et al. | |
| 2021/0077076 | A1 * | 3/2021 | Blair | A61B 8/481 |
| 2023/0024998 | A1 * | 1/2023 | Greenberg | A61B 8/4488 |
| 2023/0338754 | A1 * | 10/2023 | Agarwal | A61N 7/00 |

FOREIGN PATENT DOCUMENTS

| | | |
|---|---|---|
| KR | 10-2020-0111744 A | 9/2020 |
| KR | 10-2021-0090192 A | 7/2021 |
| KR | 10-2283276 B1 | 7/2021 |

OTHER PUBLICATIONS

M. E. Terzi et al., "Generation of a Vortex Ultrasonic Beam with a Phase Plate with an Angular Dependence of the Thickness," Moscow University Physics Bulletin, 2017, pp. 61-67, vol. 72, No. 1.

* cited by examiner

410

420

ACOUSTIC TWEEZER

CROSS-REFERENCE TO RELATED APPLICATIONS

This application claims the benefit of Korean Patent Application No. 10-2022-0117645 filed on Sep. 19, 2022, in the Korean Intellectual Property Office, the entire disclosure of which is incorporated herein by reference for all purposes.

BACKGROUND

1. Field of the Invention

One or more embodiments relate to an acoustic tweezer.

2. Description of the Related Art

An acoustic tweezer is a technology for non-contact control of the position and movement of a fine object using ultrasound. In the medical field, the acoustic tweezer is used to maximize the therapeutic effect by transferring nano-sized or micro-sized particle drugs, deoxyribonucleic acid (DNA), and cells to diseased areas. In the field of chemistry, the acoustic tweezer may be used to purify chemicals depending on particle sizes and physical properties. Because the quality of medicines, foods, cosmetics, etc., may be improved using the acoustic tweezer, studies related to acoustic tweezers have been preceded.

SUMMARY

According to an aspect, there is provided an acoustic tweezer including a function signal generator generating an arbitrary signal for an ultrasound signal, a power amplifier amplifying the ultrasound signal based on the function signal, and an ultrasound transducer of a single channel in which a hologram thin film having different thin film thicknesses for each region is attached to the oscillating surface of the ultrasound transducer, wherein the ultrasound transducer is configured to generate a plurality of ultrasound signals having different phase differences by allowing an oscillated ultrasound signal to pass through the hologram thin film.

The plurality of generated ultrasound signals may include a first ultrasound signal, a second ultrasound signal, and a third ultrasound signal, wherein the first ultrasound signal, the second ultrasound signal, and the third ultrasound signal may be configured to form an acoustic field in the form of an acoustic vortex by overlapping and interfering with each other.

The acoustic tweezer may be configured to control the movement of a target particle in a fluid using an acoustic field in the form of an acoustic vortex that is formed by ultrasound signals overlapping and interfering with each other.

The hologram thin film may be divided into n regions based on the center of the oscillating surface of the ultrasound transducer, wherein each region may have a different thin film thickness than another and wherein n may be a natural number greater than or equal to "2".

The hologram thin film may include a first region having a first thin film thickness, a second region having a second thin film thickness, and a third region having a third thin film thickness, wherein the first thin film thickness, the second thin film thickness, and the third thin film thickness may have different thin film thickness values.

The oscillating surface of the ultrasound transducer may include a fourth region to which the hologram thin film is not attached, wherein the fourth region may be a region different from the first region, the second region, and the third region.

A first ultrasound signal that passes through the first region of the hologram thin film may have a phase difference of 90 degrees (°) compared to an ultrasound signal before passing through the first region of the hologram thin film, a second ultrasound signal that passes through the second region of the hologram thin film may have a phase difference of 180° compared to an ultrasound signal before passing through the second region of the hologram thin film, and a third ultrasound signal that passes through the third region of the hologram thin film may have a phase difference of 270° compared to an ultrasound signal before passing through the third region of the hologram thin film.

The first ultrasound signal, the second ultrasound signal, and the third ultrasound signal may be simultaneously output from one oscillating surface of the ultrasound transducer.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
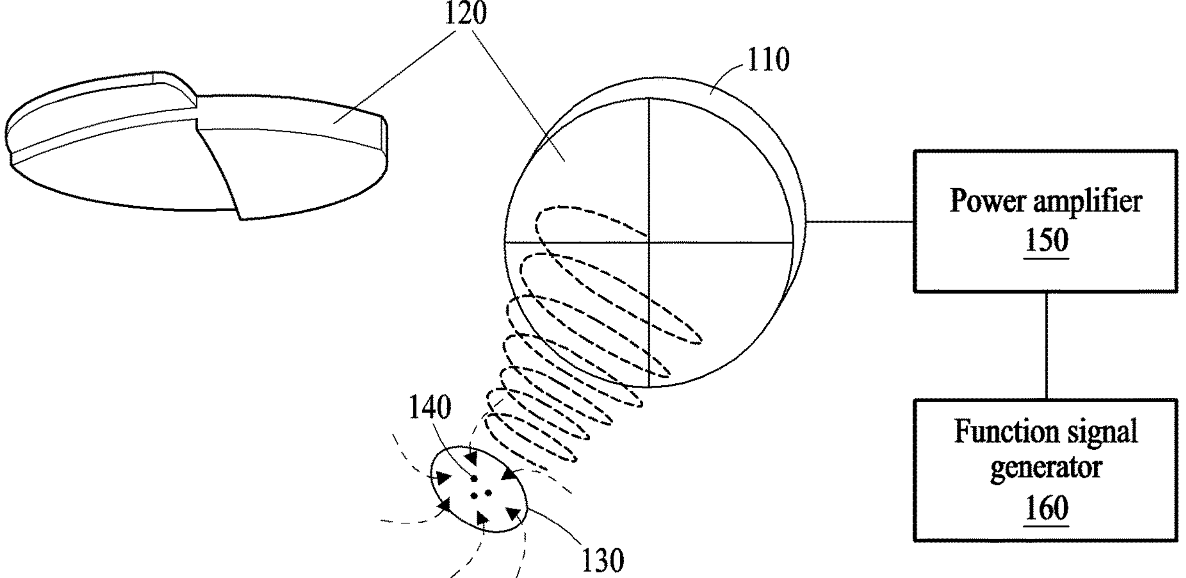
FIG. 1 is a diagram illustrating an overall overview of an acoustic tweezer according to an embodiment.

The following detailed structural or functional description is provided as an example only, and various alterations and modifications may be made to the examples. Here, examples are not construed as limited to the disclosure and should be understood to include all changes, equivalents, and replacements within the idea and the technical scope of the disclosure.

Terms, such as "first", "second", and the like, may be used herein to describe components. Each of these terminologies is not used to define an essence, order or sequence of a corresponding component but is used merely to distinguish the corresponding component from other component(s). For example, a first component may be referred to as a second component, and similarly the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a," "an," and "the" are intended to include the plural forms as well, unless the context clearly indicates otherwise. As used herein, "A or B", "at least one of A and B", "at least one of A or B", "A, B or C", "at least one of A, B and C", and "at least one of A, B, or C," each of which may include any one of the items listed together in the corresponding one of the phrases, or all possible combinations thereof. It will be further understood that the terms "comprises/including" and/or "includes/including" when used herein, specify the presence of stated features, integers, operations, operations, elements, and/or components, but do not preclude the presence or addition of one or more other features, integers, operations, operations, elements, components and/or groups thereof.

Unless otherwise defined, all terms, including technical and scientific terms, used herein have the same meaning as commonly understood by one of ordinary skill in the art to which this disclosure pertains. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

As used in connection with the present disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an example, the module may be implemented in a form of an application-specific integrated circuit (ASIC).

The term "unit" or the like used herein may refer to a software or hardware component, such as a field-programmable gate array (FPGA) or an application-specific integrated circuit (ASIC), and the "unit" performs predefined functions. However, "unit" is not limited to software or hardware. The "unit" may be configured to reside on an addressable storage medium or configured to operate one or more processors. Accordingly, the "unit" may include, for example, components, such as software components, object-oriented software components, class components, and task components, processes, functions, attributes, procedures, sub-routines, segments of program code, drivers, firmware, microcode, circuitry, data, databases, data structures, tables, arrays, and variables. The functionalities provided in the components and "units" may be combined into fewer components and "units" or may be further separated into additional components and "units." Furthermore, the components and "units" may be implemented to operate on one or more central processing units (CPUs) within a device or a security multimedia card. In addition, "unit" may include one or more processors.

Hereinafter, the examples will be described in detail with reference to the accompanying drawings. When describing the embodiments with reference to the accompanying drawings, like reference numerals refer to like elements and any repeated description related thereto will be omitted.

FIG. 1 is a diagram illustrating an overall overview of an acoustic tweezer according to an embodiment.

An acoustic tweezer described in the present disclosure may generate a plurality of ultrasound signals having different phase differences through passive phase modulation with only an ultrasound transducer of a single channel in which a hologram thin film having different thin film thicknesses for each region is attached to the surface of ultrasound transducer. The acoustic tweezer may freely control the movement of a target particle in a fluid in a three-dimensional (3D) space using an acoustic field in the form of an acoustic vortex formed by ultrasound signals overlapping and interfering with each other. The acoustic tweezer described in the present disclosure may provide a function of freely moving particles such as drugs, cells, and deoxyribonucleic acid (DNA) to a desired location in a medical field using holographic technology. The acoustic tweezer may precisely control the movement of microparticles by applying acoustic holographic technology to a focused ultrasound transducer of the single channel and forming the acoustic field in the form of the acoustic vortex. This technology does not rely on a frequency to control the size of a micro-level object, does not require a plurality of ultrasonic transducers, and does not require a multi-channel operation, so this technology may be driven by a simple system.

Referring to FIG. 1, the acoustic tweezer may include an ultrasound transducer 110, a power amplifier 150, and a function signal generator 160.

The function signal generator 160 may generate a functional arbitrary signal for an ultrasound signal. The function signal generator 160 may generate, for example, a function signal in the form of a sine wave. The function signal generator 160 may apply the generated function signal to the power amplifier 150. Here, an ultrasound irradiation condition for the acoustic tweezer may have a pressure amplitude of 300 kilopascals (kPa) to 3 megapascals (MPa), a pulse repetition frequency of 500 hertz (Hz) to 5000 kilohertz (kHz), and a pulse width of microseconds (μs) to 1 millisecond (ms).

The power amplifier 150 may amplify the ultrasound signal based on the function signal. The power amplifier 150 may amplify the ultrasound signal for the ultrasound transducer 110. The ultrasound transducer 110 may be composed of a single channel, and a hologram thin film 120 having different thin film thicknesses for each region may be attached to the oscillating surface of the ultrasound transducer 110. The ultrasound transducer 110 may generate a plurality of ultrasound signals having different phase differences by allowing an oscillated ultrasound signal to pass through the hologram thin film 120. Although the ultrasound transducer 110 is composed of a single channel, a plurality of ultrasound signals having different phase differences by allowing an ultrasound signal to pass through the hologram thin film 120 having different thin film thicknesses for each region may be generated. The ultrasound transducer 110 may have a multi-channel effect with only the single channel through the described above features. The hologram thin film 120 may include at least one of, for example, a polymer material, a resin material, and a plastic-based material.

The hologram thin film 120 may be divided into n regions based on the center of the ultrasound oscillating surface of the ultrasound transducer 110, and each region may have a different thin film thickness from another. Here, n may be a natural number greater than or equal to "2". In an embodiment of FIG. 1, the hologram thin film 120 may be divided into four regions based on the center of the ultrasound oscillating surface of the ultrasound transducer 110 but is not limited thereto and may be divided into other numbers of regions.

The hologram thin film 120 may include a first region having a first thin film thickness, a second region having a second thin film thickness, and a third region having a third thin film thickness. Here, the first thin film thickness, the second thin film thickness, and the third thin film thickness may be characterized in having different thin film thickness values.

The oscillating surface of the ultrasound transducer 110 may include a fourth region to which the hologram thin film 120 is not attached. The fourth region may be a different region from the first region, the second region, and the third region.

The plurality of generated ultrasound signals may include a first ultrasound signal, a second ultrasound signal, and a third ultrasound signal. The plurality of generated ultrasound signals according to an embodiment may include at least one of the first ultrasound signal, the second ultrasound signal, the third ultrasound signal, and a fourth ultrasound signal. The first ultrasound signal, the second ultrasound signal, and the third ultrasound signal may be characterized in being simultaneously output from one oscillating surface of the ultrasound transducer 110. That is, the first ultrasound signal, the second ultrasound signal, and the third ultrasound signal may be characterized in being simultaneously output from the oscillating surface to which the hologram thin film 120 is attached.

For example, the first ultrasound signal that passes through the first region of the hologram thin film 120 may have a phase difference of 90 degrees (°) compared to an ultrasound signal before passing through the first region of the hologram thin film 120 and the second ultrasound signal that passes through the second region of the hologram thin film 120 may have a phase difference of 180° compared to an ultrasound signal before passing through the second region of the hologram thin film 120. The third ultrasound signal that passes through the third region of the hologram thin film 120 may have a phase difference of 270° compared to an ultrasound signal before passing through the third region of the hologram thin film 120. The ultrasound signal that passes through the fourth region in which the hologram thin film 120 is not attached to the ultrasound oscillating surface of the ultrasound transducer 110 may not have a phase difference with an ultrasound signal before passing through the ultrasound transducer 110 and may also be referred to as the fourth ultrasound signal.

The first ultrasound signal, the second ultrasound signal, and the third ultrasound signal may form an acoustic field 130 in the form of an acoustic vortex by overlapping and interfering with each other. In addition, the acoustic field 130 in the form of the acoustic vortex may be formed by the first ultrasound signal, the second ultrasound signal, the third ultrasound signal, and the fourth ultrasound signal overlapping and interfering with each other. Here, the acoustic field 130 may be a ring-shaped acoustic field with "0" pressure (i.e., null pressure) at the center of the acoustic field 130. The acoustic tweezer may control the movement of a target particle 140 in a fluid using the acoustic field 130 in the form of the acoustic vortex. The controlling of the movement of the target particle 140 by the acoustic tweezer may also be expressed as picking up and moving the target particle 140. For example, the target particle 140 may be drawn into a region where the pressure is "0" while rotating like a whirlwind by the ring-shaped acoustic field and may aggregate in a cluster form, and accordingly, the movement of the target particle 140 may be controlled.

Figure 2A:
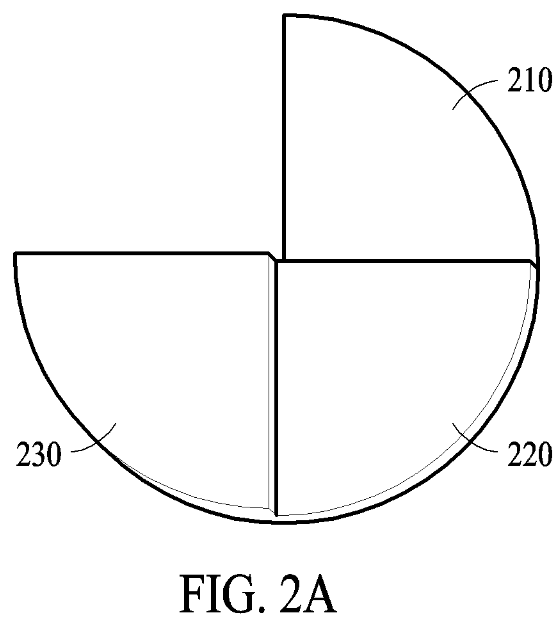
FIGS. 2A, 2B, and FIG. 3 are diagrams illustrating a hologram thin film according to an embodiment.
Figure 2B:
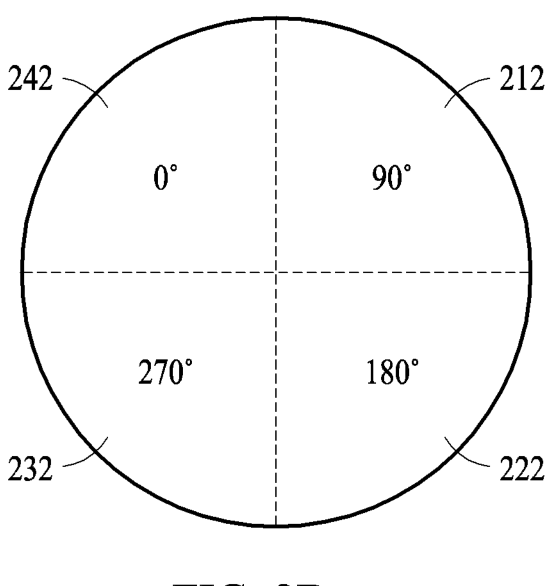
Figure 3:
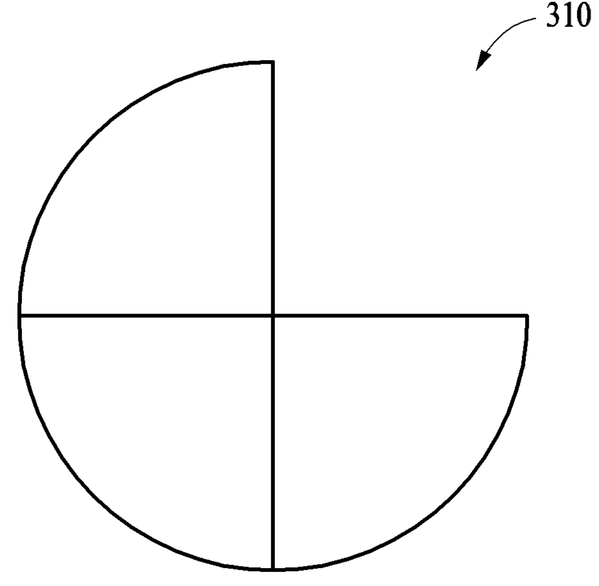
Figure 3:
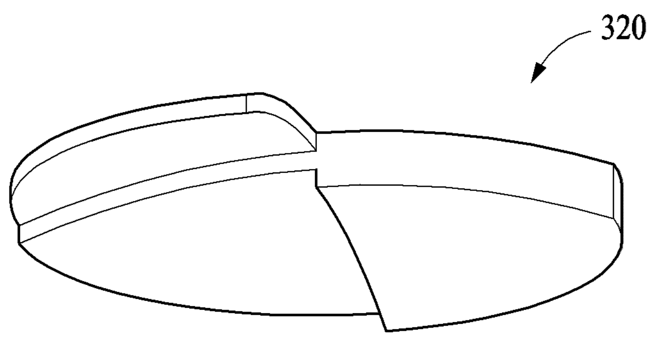

FIGS. 2A, 2B, and FIG. 3 are diagrams illustrating a hologram thin film according to an embodiment.

Referring to FIG. 2A, an example of the hologram thin film may be shown. In addition, FIG. 2B may be an example of the oscillating surface of an ultrasound transducer to which a hologram thin film is attached. In an embodiment, the hologram thin film may include a first region 210, a second region 220 and a third region 230. The first region 210 may have a first thickness, the second region 220 may have a second thickness, and the third region 230 may have a third thickness. The first thickness, the second thickness, and the third thickness may all have different thicknesses.

The first region 210 of the hologram thin film may be attached to a first region 212 of the oscillating surface of the ultrasound transducer. The second region 220 of the hologram thin film may be attached to a second region 222 of the oscillating surface of the ultrasound transducer, and the third region 230 of the hologram thin film may be attached to a third region 232 of the oscillating surface of the ultrasound transducer. In addition, the hologram thin film may not be attached to a fourth region 242 of the oscillating surface of the ultrasound transducer. Therefore, the fourth ultrasound signal that passes through the fourth region 242 of the oscillating surface of the ultrasound transducer may not have a phase difference with the ultrasound signal before the ultrasound signal passes through the fourth region 242 of the oscillating surface of the ultrasound transducer.

The first ultrasound signal that passes through the first region 212 of the oscillating surface of the ultrasound transducer to which the first region 210 of the hologram thin film is attached may have a phase difference of 90° compared to the ultrasound signal before passing through the first region 212 of the oscillating surface of the ultrasound transducer. In addition, the second ultrasound signal that passes through the second region 222 of the oscillating surface of the ultrasound transducer to which the second region 220 of the hologram thin film is attached may have a phase difference of 180° compared to the ultrasound signal before passing through the second region 222 of the oscillating surface of the ultrasound transducer. The third ultrasound signal that passes through the third region 232 of the oscillating surface of the ultrasound transducer to which the third region 230 of the hologram thin film is attached may have a phase difference of 270° compared to the ultrasound signal before passing through the third region 232 of the oscillating surface of the ultrasound transducer. Since the first ultrasound signal, the second ultrasound signal, the third ultrasound signal, and the fourth ultrasound signal have different phase differences, interference may occur between the first ultrasound signal, the second ultrasound signal, the third ultrasound signal, and the fourth ultrasound signal, and the acoustic field in the form of the acoustic vortex may be formed by the interference.

The phase may change depending on the acoustic properties of the hologram thin film. The phase difference ($\Delta\theta$) by the hologram thin film may be calculated based on Equation 1.

$$\Delta\theta = |k_m - k_0|t_h \quad \text{[Equation 1]}$$

$$k = \frac{2\pi}{\lambda}$$

$$\lambda = \frac{c}{f}$$

Here, $k_m$ may denote a wavenumber of material, $k_0$ may denote a wavenumber of medium, and $t_h$ may denote the thickness of the material, that is, the thickness of the hologram thin film. f may denote a central frequency of an ultrasound, and c may denote the speed of sound of the hologram thin film or fluid. The phase difference may be determined based on at least one of the frequency of the ultrasound, the speed of sound of the hologram thin film, and the thickness of the hologram thin film. The thickness of the hologram thin film may be determined based on the acoustic properties of the hologram thin film.

In an embodiment, a structure range of the ultrasound transducer of a single channel may have a diameter of 1 millimeter (mm) to 1000 mm and a radius of curvature of 1 mm to 1500 mm. Based on the diameter and radius of curvature of the ultrasound transducer, the total diameter of the hologram thin film may be 1 mm to 1000 mm and the radius of curvature of the hologram thin film may be 1 mm to 1500 mm.

A reference numeral 310 of FIG. 3 may be a plane view of the hologram thin film. The reference numeral 310 may be, for example, a drawing in which the hologram thin film is viewed from a concave surface. In addition, a reference numeral 320 of FIG. 3 may be a perspective view of the hologram thin film. Referring to the reference numeral 320, it may be seen that the thin film thickness is different for each region of the hologram thin film. Accordingly, the ultrasound transducer may generate the plurality of ultrasound signals having different phase differences with only the single channel.

Figure 4:
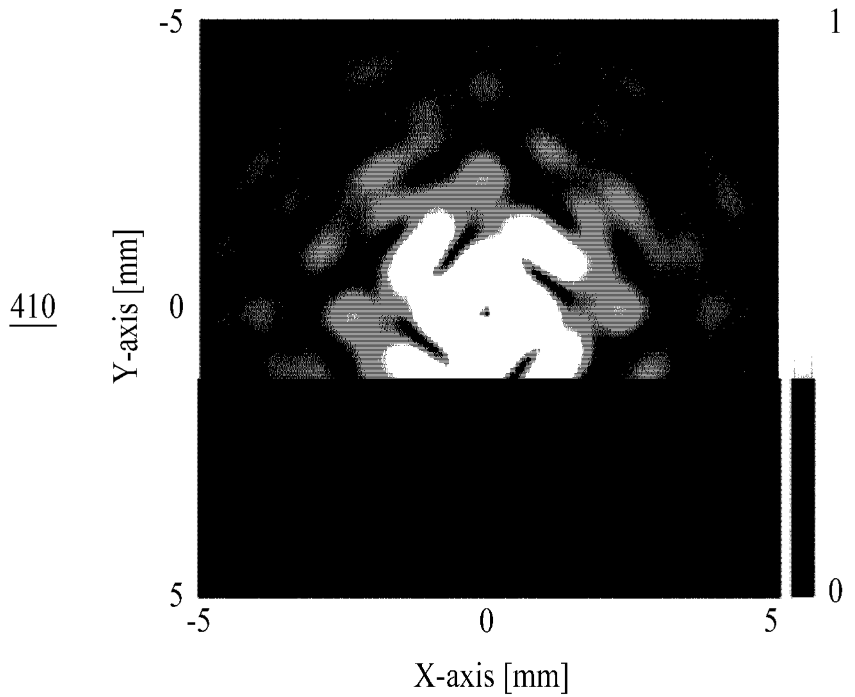
FIG. 4 is a diagram illustrating an acoustic beam field in the form of an acoustic vortex according to another embodiment.
Figure 4:
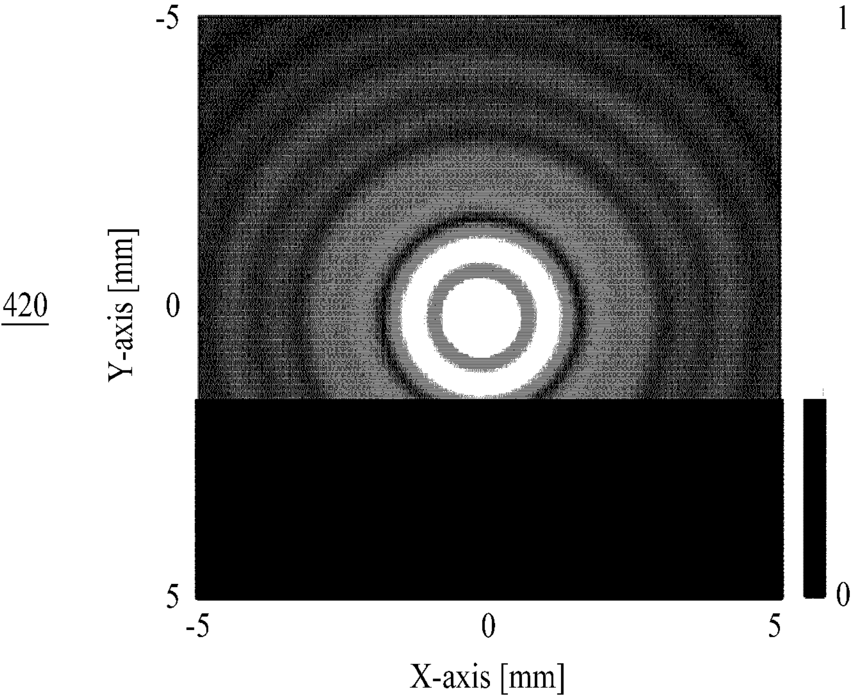

FIG. 4 is a diagram illustrating the acoustic field in the form of the acoustic vortex according to another embodiment.

A reference numeral 410 may be a case in which the hologram thin film having different thin film thicknesses for each region is attached to the focused ultrasound transducer, and a reference numeral 420 may be a case in which hologram thin film is not attached to the focused ultrasound transducer.

Referring to the reference numeral 410, it may be seen that, unlike the reference numeral 420, the acoustic field in the form of the acoustic vortex is formed by overlapping and interfering with the ultrasound signals. Referring to the reference numeral 420, it may be seen that the acoustic field in the form of a circle that is focused on one point by overlapping the ultrasound signals without destructive interference is formed.

In the acoustic tweezer described in the present disclosure, the hologram thin film having different thin film thicknesses for each region is attached to the ultrasound transducer to generate the plurality of ultrasound signals having different phase differences, and accordingly, the acoustic field in the form of the acoustic vortex such as the reference numeral 410 may be formed. The acoustic tweezer may control the movement of the target particle in the fluid using the acoustic field in the form of the acoustic vortex formed by ultrasound signals overlapping and interfering with each other. In an embodiment of FIG. 4, each region of the hologram thin film may be a hologram thin film made of the polymer material that is divided into three parts, and the thickness of each region may be consistently "1", "2", and "3" times based on the thickness of one region. In this case, the whirlwind, that is, the acoustic field in the form of the acoustic vortex, may be formed.

Figure 5:
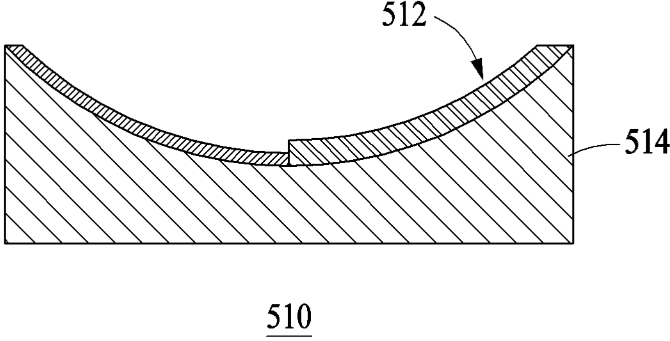
FIG. 5 is a diagram illustrating a shape of a hologram thin film according to a shape of an ultrasound transducer according to another embodiment.
Figure 5:
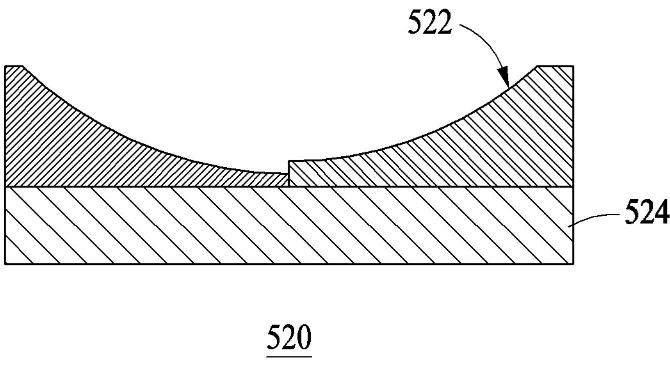

FIG. 5 is a diagram illustrating a shape of the hologram thin film according to a shape of the ultrasound transducer according to another embodiment.

Referring to FIG. 5, a shape of the hologram thin film may be determined based on a shape of the ultrasound transducer. A reference numeral 510 may show an example in which an ultrasound transducer 514 is a focused ultrasound transducer and has a concave shape. In addition, a reference numeral 520 may show an example in which an ultrasound transducer 524 is a plane ultrasound transducer and has a flat shape.

When the ultrasound transducer 514 has the concave shape as shown in the reference numeral 510, a hologram thin film 512 may be attached to the focused ultrasound transducer (the ultrasound transducer 514). In this case, an ultrasound focal length may be determined based on the radius of curvature of the focused ultrasound transducer (the ultrasound transducer 514).

When the ultrasound transducer 524 is plane, as shown in the reference numeral 520, a hologram structure 522 having different steps may be attached to the plane ultrasound transducer (the ultrasound transducer 524). The hologram structure 522 (or may also be referred to as a hologram thin film) may be formed in a concave shape to generate the phase difference between the ultrasound signals, and accordingly, the acoustic field in the form of the acoustic vortex may be formed. In the case of the plane ultrasound transducer (the ultrasound transducer 524), the ultrasound focal length may be determined based on the radius of curvature of the hologram structure 522.

Figure 6:
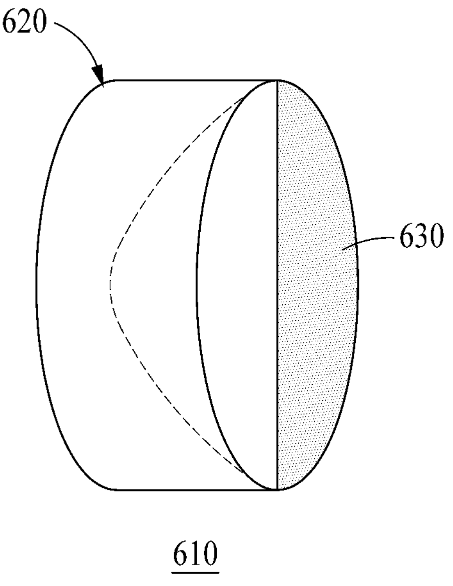
FIG. 6 is a diagram illustrating a focused ultrasound beam pattern with bifocal formed by a hologram thin film according to another embodiment.
Figure 6:
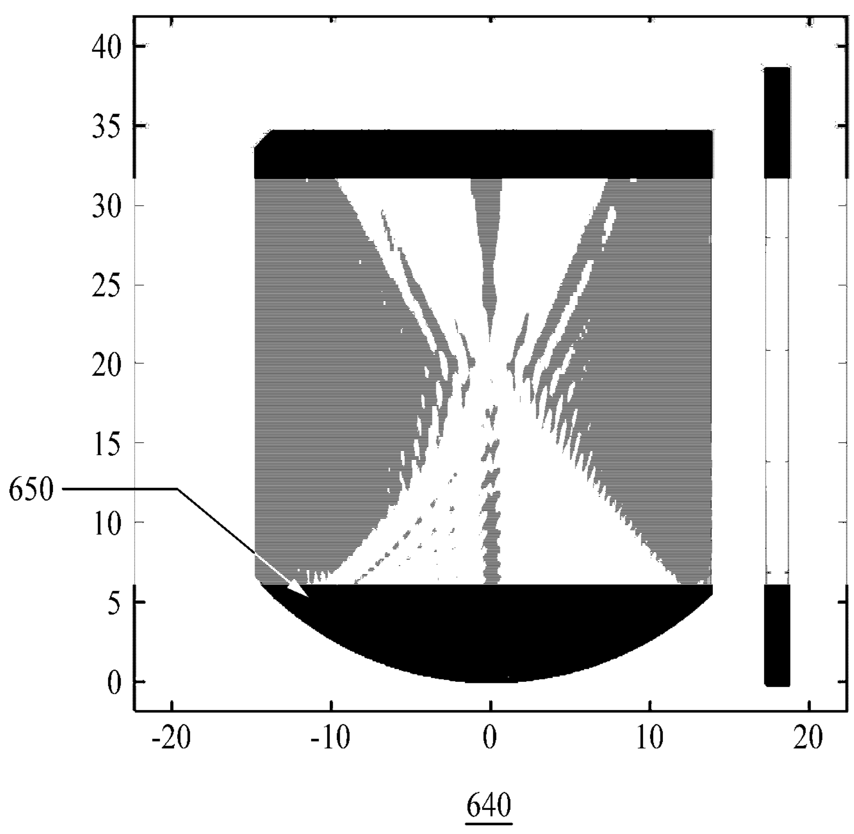

FIG. 6 is a diagram illustrating a focused ultrasound beam pattern with bifocal formed by the hologram thin film according to another embodiment.

A reference numeral 610 may show an example in which ½ of an area of an ultrasound transducer 620 of a single channel is attached with a hologram thin film 630. Here, the hologram thin film 630 may have a thickness of 1 mm in the case of a 2 MHz ultrasound frequency and may be a polymer material. A structural characteristic of the hologram thin film 630 may be based on Equation 1. The ultrasound transducer 620 may be in a state in which half is coated with the hologram thin film 630 made of the polymer material, and the other half is coated with nothing. A reference numeral 640 may show a beam pattern generated by the ultrasound transducer 620. The ultrasound transducer 620 attached with the hologram thin film 630 may form two focal points. A reference numeral 650 in the reference numeral 640 may be a hologram thin film attached to the ultrasound transducer 620. Contrary to the above description, when the hologram thin film is not attached with the ultrasound transducer, one focal point may be formed.

Therefore, the acoustic tweezers in which the hologram thin film 630 is attached to the ultrasound transducer 620 may form a bifocal even with the ultrasound transducer of a single channel when holographic technology is used. The feature that the focused ultrasound with the bifocal may be generated through acoustic holographic technology may be utilized as low-intensity focused ultrasound (LIFU) brain stimulation or high-intensity focused ultrasound (HIFU) tissue disruption applications simultaneously at two points in future treatment fields using the HIFU and the LIFU.

Figure 7:
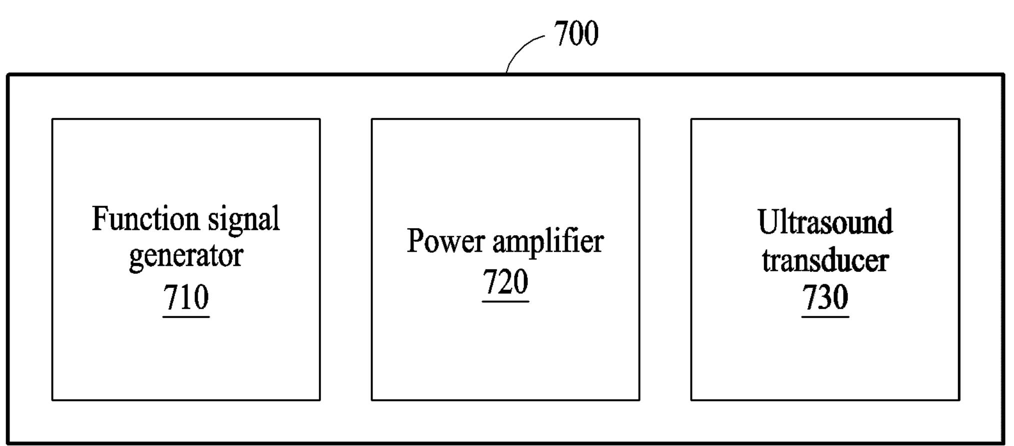
FIG. 7 is a block diagram illustrating a configuration of an acoustic tweezer according to an embodiment.

FIG. 7 is a block diagram illustrating a configuration of an acoustic tweezer according to an embodiment.

Referring to FIG. 7, an acoustic tweezer 700 may include a function signal generator 710, a power amplifier 720, and an ultrasound transducer 730. The acoustic tweezer 700 may correspond to the acoustic tweezer described in the present disclosure, and the function signal generator 710 may correspond to the function signal generator described in the present disclosure. In addition, the power amplifier 720 may correspond to the power amplifier described in the present disclosure, and the ultrasound transducer 730 may correspond to the ultrasound transducer described in the present disclosure.

The function signal generator 710 may generate the arbitrary functional signal for the ultrasound signal. In addition, the power amplifier 720 may amplify the ultrasound signal based on the function signal. The ultrasound transducer 730 may have a hologram thin film having different thin film thicknesses for each region that is attached to the oscillating surface of the ultrasound transducer 730 and may be the single channel. The ultrasound transducer 730 may generate the plurality of ultrasound signals having different phase differences by allowing an oscillated ultrasound signal to pass through the hologram thin film.

According to an embodiment of the present disclosure, the precise spatial control for microparticles may be possible by applying acoustic holographic technology to the focused ultrasound transducer of a single channel and forming the acoustic field in the form of the acoustic vortex.

According to an embodiment of the present disclosure, unlike an acoustic tweezer according to the related art, since the present disclosure may control the movement of microparticles with only a low frequency and the ultrasound transducer of a single channel, a structure of the acoustic tweezer may be simplified compared to the acoustic tweezer according to the related art, and the degree of acoustic attenuation in tissue due to the low frequency may be lowered, so utilization may be improved and cost may be reduced.

According to an embodiment of the present disclosure, since the holographic technology is applied to the focused ultrasound transducer, acoustic pressure may be focused on the focal point and spatial resolution may be high. Due to the strong attraction of the generated acoustic vortex, the force to hold particles of the present disclosure may be stronger than related technologies even with a pressure amplitude that does not damage soft tissue.

According to an embodiment of the present disclosure, since passive phase modulation is possible by replacing only the hologram thin film on the ultrasound transducer of a single channel, the present disclosure may substitute the function of a multi-channel ultrasound transducer that performs active phase modulation.

The above-described devices may be configured to act as one or more software modules in order to perform the operations of the above-described examples, or vice versa.

As described above, although the examples have been described with reference to the limited drawings, a person skilled in the art may apply various technical modifications and variations based thereon. For example, suitable results may be achieved if the described techniques are performed in a different order and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. An acoustic tweezer comprising:

a function signal generator configured to generate a function signal for an ultrasound signal;

a power amplifier configured to amplify the ultrasound signal based on the function signal; and an ultrasound transducer of a single electrical driving channel in which a hologram thin film having different thin film thicknesses for each region is attached to a concave ultrasound oscillating surface of the ultrasound transducer, wherein the ultrasound transducer is configured to generate a plurality of ultrasound signals having different phase differences simultaneously from the single electrical driving channel by allowing a primary ultrasound signal oscillated from the single electrical driving channel to pass through the different thicknesses of the respective regions of the hologram thin film to induce a passive physical propagation delay within a medium of the hologram thin film, wherein the ultrasound transducer is a focused ultrasound transducer having a concave ultrasound oscillating surface, wherein the hologram thin film is conformally attached to the concave ultrasound oscillating surface as a single integrated passive layer, and wherein an ultrasound focal length is determined based on a radius of curvature of the concave ultrasound oscillating surface.

2. The acoustic tweezer of claim 1, wherein the plurality of generated ultrasound signals comprises a first ultrasound signal, a second ultrasound signal, and a third ultrasound signal, wherein the first ultrasound signal, the second ultrasound signal, and the third ultrasound signal are configured to form an acoustic field in the form of an acoustic vortex by overlapping and interfering with each other at a focal point determined by the radius of curvature of the concave ultrasound oscillating surface.

3. The acoustic tweezer of claim 1, wherein the acoustic tweezer is configured to control movement of a target particle in a fluid using an acoustic field in the form of an acoustic vortex that is formed by the passive physical propagation delay induced by the different thicknesses of the hologram thin film.

4. The acoustic tweezer of claim 1, wherein the hologram thin film is divided into n regions based on a center of the concave ultrasound oscillating surface of the ultrasound transducer, wherein each region has a different thin film thickness than another to induce a specific amount of propagation delay relative to each other, wherein n is a natural number greater than or equal to “2”.

5. The acoustic tweezer of claim 1, wherein the hologram thin film comprises a first region having a first thin film thickness, a second region having a second thin film thickness, and a third region having a third thin film thickness, wherein the first thin film thickness, the second thin film thickness, and the third thin film thickness have different thin film thickness values corresponding to pre-calculated acoustic phase shifts.

6. The acoustic tweezer of claim 5, wherein the concave ultrasound oscillating surface of the ultrasound transducer comprises a fourth region to which the hologram thin film is not attached, wherein the fourth region is a region different from the first region, the second region, and the third region.

7. The acoustic tweezer of claim 6, wherein;

a first ultrasound signal that passes through the first region of the hologram thin film has a phase difference of 90 degrees compared to an ultrasound signal passing through the fourth region where the hologram thin film is not attached, a second ultrasound signal that passes through the second region of the hologram thin film has a phase difference of 180° compared to the ultrasound signal passing through the fourth region, and a third ultrasound signal that passes through the third region of the hologram thin film has a phase difference of 270° compared to the ultrasound signal passing through the fourth region.

8. The acoustic tweezer of claim 7, wherein the first ultrasound signal, the second ultrasound signal, and the third ultrasound signal are simultaneously output from the same continuous concave ultrasound oscillating surface of the single electrical driving channel.

* * * * *